United States Patent
Iizuka et al.

(10) Patent No.: US 10,825,233 B2
(45) Date of Patent: Nov. 3, 2020

(54) IMAGE PROCESSING APPARATUS

(71) Applicant: CANON KABUSHIKI KAISHA, Tokyo (JP)

(72) Inventors: Naoya Iizuka, Yokohama (JP); Kenichi Nagae, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/270,408

(22) Filed: Feb. 7, 2019

(65) Prior Publication Data

US 2019/0251736 A1    Aug. 15, 2019

(30) Foreign Application Priority Data

Feb. 13, 2018    (JP) ................. 2018-023554

(51) Int. Cl.
| | |
|---|---|
| G06T 9/00 | (2006.01) |
| G06T 11/00 | (2006.01) |
| G06T 15/08 | (2011.01) |
| A61B 5/00 | (2006.01) |
| G06T 15/20 | (2011.01) |

(52) U.S. Cl.
CPC ............ *G06T 15/08* (2013.01); *A61B 5/0095* (2013.01); *A61B 5/7425* (2013.01); *G06T 9/00* (2013.01); *G06T 11/006* (2013.01); *G06T 11/008* (2013.01); *G06T 15/20* (2013.01); *A61B 2576/00* (2013.01); *G06T 2207/20221* (2013.01); *G06T 2210/41* (2013.01); *G06T 2211/421* (2013.01)

(58) Field of Classification Search
CPC ..... A61B 5/0095; A61B 5/0073; A61B 6/032; A61B 6/037; A61B 5/0071; A61B 5/055; A61B 5/0507; A61B 5/0512; A61B 6/481; A61B 6/486; A61B 5/0522; A61B 6/48–488; G06T 7/0012; G06T 9/00; G06T 11/008; G06T 2207/10072–10112; G06T 2207/10132; G06T 2207/10136; G06T 2207/30034; G06K 9/52
See application file for complete search history.

(56) References Cited

U.S. PATENT DOCUMENTS

| | | | |
|---|---|---|---|
| 6,573,855 B1 * | 6/2003 | Hayakawa | G01S 13/88 342/176 |
| 2004/0175048 A1 * | 9/2004 | Pearlman | G06T 9/00 382/232 |
| 2007/0036442 A1 * | 2/2007 | Stoffer | G06T 9/00 382/232 |

FOREIGN PATENT DOCUMENTS

JP    2014-68701 A    4/2014

OTHER PUBLICATIONS

Chernoglazov, Alexander Igorevich. "Improving visualisation of large multi-variate datasets: New hardware-based compression algorithms and rendering techniques." (2012) (Year: 2012).*

(Continued)

*Primary Examiner* — Diane M Wills
(74) *Attorney, Agent, or Firm* — Canon U.S.A., Inc. IP Division (57) ABSTRACT

An image processing apparatus acquires volume data including a negative voxel value and derived from a photoacoustic wave produced by irradiating a subject with light, generates compressed volume data by compressing the volume data to selectively reduce a data amount of voxel data having a voxel value whose absolute value is less than a threshold, and saves the compressed volume data.

13 Claims, 6 Drawing Sheets

(56) References Cited

OTHER PUBLICATIONS

Sandbichler, Michael, et al. "A novel compressed sensing scheme for photoacoustic tomography." SIAM Journal on Applied Mathematics 75.6 (2015): 2475-2494. (Year: 2015).*

* cited by examiner

IMAGE PROCESSING APPARATUS

BACKGROUND

Field

The present disclosure relates to an image processing technology for medical image data.

Description of the Related Art

A modality apparatus is known that acquires information about characteristics of inside of a subject by detecting a photoacoustic wave that is produced by irradiating the subject with light. Japanese Patent Application Laid-Open No. 2014-68701 describes generating three-dimensional volume data based on a photoacoustic signal that is a received signal of a photoacoustic wave.

SUMMARY

According to an aspect of the present disclosure, an image processing apparatus comprises a processor configured to execute a program that causes the image processing apparatus to acquire volume data including a negative voxel value and derived from a photoacoustic wave produced by irradiating a subject with light, generate compressed volume data by compressing the volume data to selectively reduce a data amount of voxel data having a voxel value whose absolute value is less than a threshold, and save the compressed volume data.

Further feature will become apparent from the following description of exemplary embodiments with reference to the attached drawings.

DESCRIPTION OF THE EMBODIMENTS

A first exemplary embodiment of the present disclosure will be described in detail below with reference to the drawings. As a rule, the same components are provided with the same reference numbers and redundant description thereof will be omitted. Detailed features such as a computational expression and a computational procedure to be described below can be appropriately modified depending on a configuration of an apparatus to which an embodiment of the present disclosure is applied and various conditions, and are not intended to limit the scope of the present disclosure to the following description.

Figure 1:
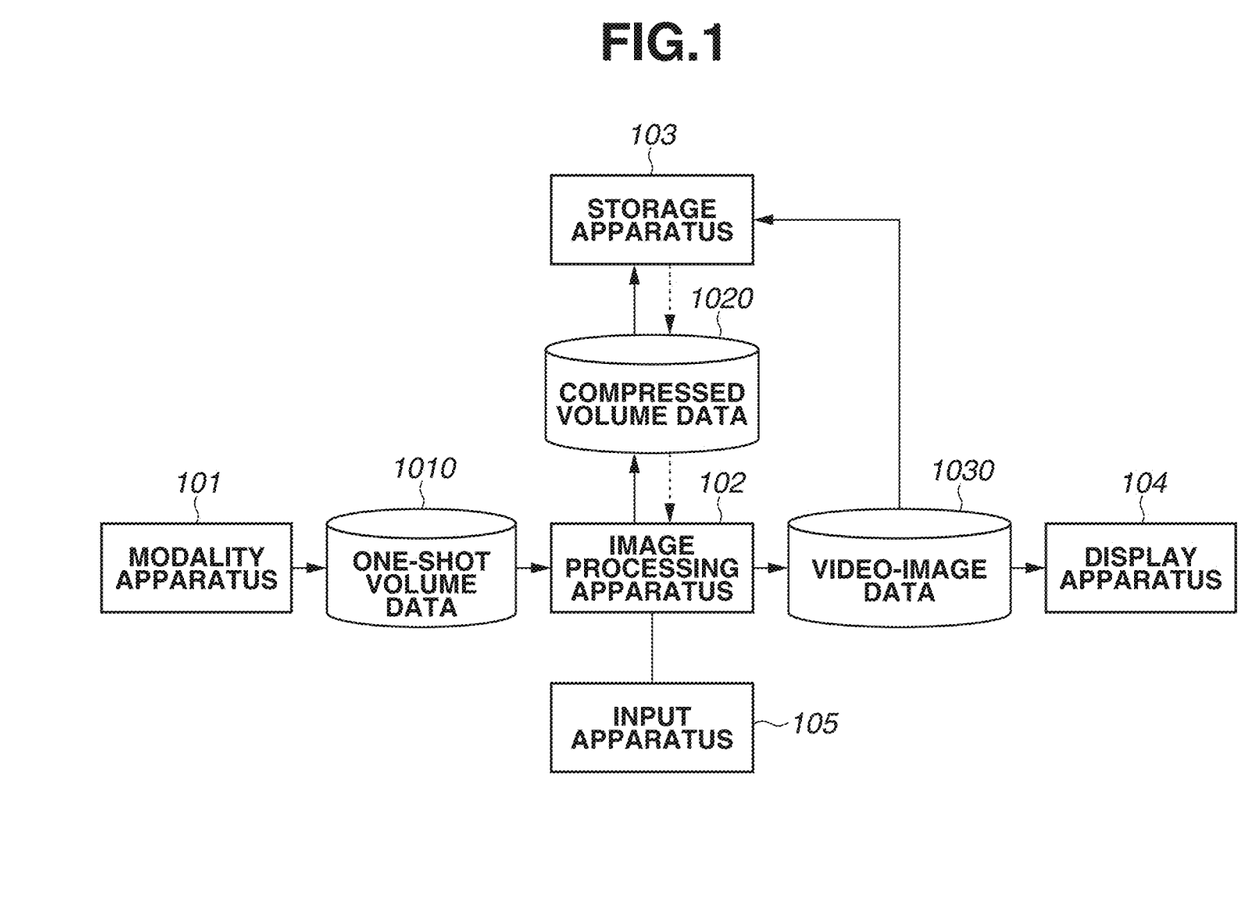
FIG. 1 is a block diagram illustrating apparatuses included in a system according to a first exemplary embodiment and data to be exchanged between the apparatuses.

FIG. 1 illustrates a system according to the present exemplary embodiment. This system includes a modality apparatus (a medical image capturing apparatus) 101, an image processing apparatus 102, a storage apparatus 103, and a display apparatus 104.

The modality apparatus 101 generates three-dimensional medical image data (hereinafter referred to as "one-shot volume data") 1010 of a subject by capturing an image of the subject, and outputs the generated one-shot volume data 1010 to the image processing apparatus 102. The one-shot volume data 1010 is obtained for each light irradiation.

The modality apparatus 101 is an apparatus such as a photoacoustic imaging apparatus, a piece of ultrasonic diagnostic equipment, a magnetic resonance imaging (MRI) apparatus, or an X-ray computed tomography (CT) apparatus. In the present exemplary embodiment, the photoacoustic imaging apparatus is adopted as the modality apparatus, which will be described below. The photoacoustic imaging apparatus is an apparatus that generates information indicating a characteristic value corresponding to each of a plurality of positions within a subject, using a received signal which is obtained by receiving a photoacoustic wave produced by light irradiation. In other words, the photoacoustic imaging apparatus is an apparatus that generates a three-dimensional space distribution of characteristic value information derived from a photoacoustic wave, as three-dimensional medical image data (volume data). Because the three-dimensional volume data has a large data size, a load put on a storage in storing the three-dimensional volume data is large. For example, in a case where the three-dimensional volume data is to be converted into a video, a load put on the storage is enormous if the volume data for video frames is saved as the original data. The system according to the present exemplary embodiment is devised in view of such an issue, and is directed to reduction of the volume of the saved three-dimensional volume data.

The three-dimensional medical image data generated by the photoacoustic imaging apparatus reflects an absorption amount and an absorption rate of optical energy. Examples of the three-dimensional medical image data generated by the photoacoustic imaging apparatus include a sound pressure (an initial sound pressure) of a generated acoustic wave, an optical energy absorption density, a light absorption coefficient, and information about the concentration of a substance constituting a tissue. Examples of the information about the concentration of the substance include oxygen saturation in blood, a total hemoglobin concentration, and an oxyhemoglobin or deoxyhemoglobin concentration. The examples of the information about the concentration of the substance can further include a glucose concentration, a collagen concentration, a melanin concentration, and a volume fraction of fat or water.

The storage apparatus 103 can be a computer readable storage medium such as a read only memory (ROM), a magnetic disk, or a flash memory. The storage apparatus 103 can be a storage server connected via a network, such as a picture archiving and communication system (PACS).

The image processing apparatus 102 acquires a plurality of pieces of one-shot volume data 1010 from the modality apparatus 101. These pieces of one-shot volume data 1010 are each obtained at different positions for each light irradiation. The image processing apparatus 102 extracts voxel data having a voxel value whose absolute value is large, from among voxel data of the pieces of one-shot volume data 1010. The image processing apparatus 102 thereby generates pieces of volume data 1020 in which a data amount of the one-shot volume data 1010 is compressed. In other words, the image processing apparatus 102 compresses the above-described volume data to selectively reduce the data amount of voxel data having a voxel value whose absolute value is less than a threshold. The image processing apparatus 102 performs compression by selectively using voxel data having a voxel value whose absolute value is large. The image processing apparatus 102 performs compression without using voxel data having a voxel value whose absolute value is small. For example, the image processing apparatus 102 can compress volume data by extracting voxel data having a voxel value whose absolute value is greater than a predetermined threshold. In other words, the image processing apparatus 102 can compress volume data by reducing the data amount of voxel data having a voxel value whose absolute value is less than a predetermined threshold. In this process, the image processing apparatus 102 can compress the data amount by deleting voxel data having a voxel value whose absolute value is less than a predetermined threshold or performing processing such as interpolation processing.

Here, such threshold processing for the absolute value of a voxel value is executed in order to extract voxel data having a positively large value and voxel data having a negatively large value. Therefore, the image processing apparatus 102 can compress volume data by extracting voxel data having a voxel value greater than a first threshold that is positive, and voxel data having a voxel value less than a second threshold that is negative. In this case, the image processing apparatus 102 compresses the above-described volume data to selectively reduce the data amount of voxel data having a voxel value less than the first threshold that is positive and greater than the second threshold that is negative. The absolute value of the first threshold and that of the second threshold can be identical or can be different. If the absolute value of the first threshold and that of the second threshold are identical, this case is equivalent to the case where the threshold processing is performed for the absolute value of a voxel value.

A voxel having a voxel value equal to the threshold can be handled as an extraction target, or can be handled as a data-amount reduction target.

In the volume data generated by the photoacoustic imaging apparatus, a positive-value voxel and a negative-value voxel tend to appear equally. Therefore, with respect to the volume data generated by the photoacoustic imaging apparatus, advantageous information can be selectively extracted by setting a threshold for the absolute value of a voxel value, without setting a threshold for each of a positive value and a negative value separately.

The storage apparatus 103 stores the generated pieces of compressed volume data 1020.

The image processing apparatus 102 generates synthetic volume data by synthesizing the plurality of pieces of compressed volume data 1020 stored in the storage apparatus 103. The image processing apparatus 102 generates a maximum intensity projection image by performing maximum intensity projection for the generated synthetic volume data in a specific direction.

The image processing apparatus 102 generates video-image data 1030, by arranging the generated maximum intensity projection images in chronological order of image capturing. The display apparatus 104 updates display of images based on the generated video-image data 1030 sequentially, thereby displaying the images as a video. The image processing apparatus 102 can serve as a display control unit that causes the display apparatus 104 to display an image based on the video-image data 1030.

With the above-described configuration, the one-shot volume data 1010 generated by the modality apparatus 101 for display of a video can be compressed, and the compressed volume data can be stored in the storage apparatus 103.

As described above, in the present exemplary embodiment, among the one-shot volume data including a negative value, the voxel data having a voxel value whose absolute value is large is extracted, and the extracted voxel data is compressed, so that the compressed volume data including a negative value whose absolute value is high is generated. Since the compressed volume data including the negative value is used in generating the synthetic volume data, the negative value offsets an artifact component, and an artifact of the synthetic volume data is inhibited.

As a comparative example, assume a case where one-shot volume data is compressed by extracting voxel data having a large voxel value. In this case, information indicating a negative value of the one-shot volume data is lost by data compression processing. Therefore, in the compression method of the comparative example, offsetting an artifact by a negative value cannot be performed when synthetic volume data is generated. Hence, the effect of inhibiting the artifact of the synthetic volume data declines.

A video condition (a condition for generating a video from a one-shot volume data set, such as an area and a direction in creating a maximum intensity projection image, and the number of pieces of one-shot volume data to be used for synthesis) can be changed. When generating a video again based on a different condition, the image processing apparatus 102 reads out the plurality of pieces of compressed volume data 1020 saved in the storage apparatus 103. The image processing apparatus 102 then performs restoration for these pieces of data as necessary. Afterward, the image processing apparatus 102 generates the synthetic volume data, and then generates the video-image data 1030.

Figure 2:
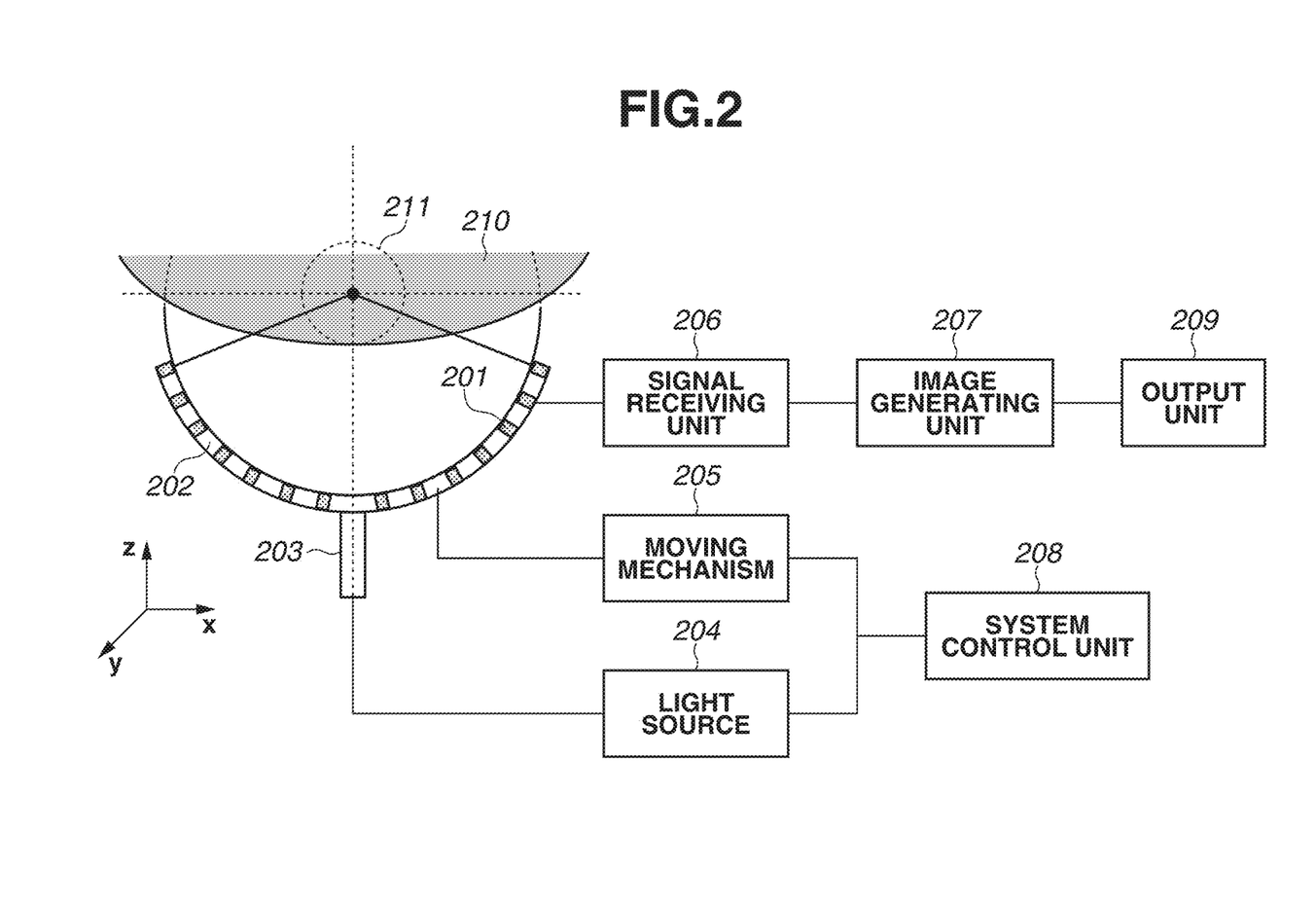
FIG. 2 is a block diagram illustrating a modality apparatus according to the first exemplary embodiment.

Next, the modality apparatus 101 according to the present exemplary embodiment will be described with reference to FIG. 2. The modality apparatus 101 to be described here is a photoacoustic imaging apparatus.

The photoacoustic imaging apparatus has a probe 202, an irradiation optical system 203, a light source 204, a moving mechanism 205, a signal receiving unit 206, an image generating unit 207, a system control unit 208, and an output unit 209. The probe 202 has a plurality of transducers 201.

The probe 202 includes the plurality of transducers 201 that are arrayed. The transducer 201 detects a photoacoustic wave propagating from a subject 210, and converts the detected photoacoustic wave into an electrical signal (hereinafter may also be referred to as "photoacoustic signal"). The transducer 201 can be implemented using any type of element, including an element using a piezoelectric phenomenon, an element using resonance of light, and an element using a change in electrostatic capacitance. The transducer 201 is not limited to these elements, and any type of element can be used if the element can receive an acoustic wave. In the present exemplary embodiment, the probe 202 has an internal surface shaped like a hemisphere, and the plurality of transducers 201 has the respective acoustic wave detection surfaces that are disposed along this shape. Axes each extending along a direction of higher receiving sensitivity of the transducer 201, i.e., directional axes, are thereby concentrated at a point near the center of the hemisphere. For example, an axis extending along the direction of the normal to the receiving surface of the transducers 201 can be the directional axis. In a high resolution area 211, the directions of higher receiving sensitivity of the transducers 201 are concentrated. From the high resolution area 211, subject information that is more accurate than those of other areas can be acquired. The shape of the probe 202 is not limited to the hemisphere. The probe 202 can have a shape of an ellipse that is taken along any cross section, or can be configured of a polyhedron. Even if the probe 202 has such other shapes, the probe 202 can be configured such that the directions of higher receiving sensitivity of the transducers 201 are concentrated in a predetermined area. Further, the probe 202 can support the plurality of transducers 201 one-dimensionally or two-dimensionally. In this way, the probe 202 having the plurality of transducers 201 that is multidimensionally disposed is used. Using such a probe, acoustic waves can be simultaneously received at a plurality of positions, and thus, the measurement time can be reduced. In the configuration of the present exemplary embodiment, the center of the probe 202 which is shaped like a hemisphere is the position where the receiving sensitivity is highest. Therefore, it is conceivable that the high resolution area 211 is a spherical area spread+isotropically from the center of the hemisphere.

The light source 204 emits light based on a control signal transmitted from the system control unit 208. The shape of the light emitted from the light source 204 is deformed by the irradiation optical system 203, and the subject 210 is irradiated with the deformed light. The light emitted by the light source 204 can be pulsed light having a pulse width of about 10 nsec to 100 nsec. This can effectively produce a photoacoustic wave. For the light source 204, a laser can be adopted, from which a high output is obtainable so that light reaches a deep part of the subject 210. However, the light source 204 is not limited to the laser. A component such as a light emitting diode or a flash lamp can be used in place of the laser. Various types of laser are applicable to the light source 204, including a solid-state laser, a gas laser, a dye laser, and a semiconductor laser. The wavelength of the light generated by the light source 204 can be a length that enables the light to propagate to the inside of the subject 210. For example, in a case where the subject 210 is a living body, the wavelength of the light generated by the light source 204 can be 500 nm or more and 1200 nm or less. Further, the laser to be used for the light source 204 can be a laser that produces a strong output and can continually change a wavelength. Examples of such a laser include a Ti:sa laser of Nd:YAG excitation, and an alexandrite laser. Moreover, the light source 204 can be configured to include a plurality of single-wavelength lasers of different wavelengths.

The light emitted from the light source 204 is transmitted to the irradiation optical system 203 via a transmission system. The irradiation optical system 203 is a light irradiation unit. An optical absorber such as blood within the subject 210 produces a photoacoustic wave by absorbing the optical energy with which the subject 210 is irradiated as described above. For the transmission system, for example, a system configured by connecting a plurality of hollow waveguides using a joint equipped with a mirror can be used. In this system, an articulated arm is configured so that the light can propagate through the waveguides. The articulated arm and optical elements such as a mirror and a lens enable the light to propagate through space. The transmission system can be configured of bundle fiber.

The signal receiving unit 206 performs processing such as sampling processing and amplification processing on a reception signal output from each of the plurality of transducers 201, thereby converting the reception signal into a digital signal. The signal receiving unit 206 sends the digital signal to the image generating unit 207. The signal receiving unit 206 is configured to include a signal amplifier such as an operation amplifier, and an analog/digital converter (ADC).

The image generating unit 207 generates volume data by performing image reconstruction processing, using the digital signal sent from the signal receiving unit 206.

The moving mechanism 205 moves the probe 202 including the transducers 201, relative to the subject 210. The moving mechanism 205 serves to change the relative position between the probe 202 and the subject 210. Therefore, the moving mechanism 205 can move the subject 210 while fixing the position of the probe 202. The relative position between the probe 202 and the subject 210 can be changed by moving both of the probe 202 and the subject 210. The moving mechanism 205 is configured of a movable stage that moves the probe 202 relative to the subject 210. The moving mechanism 205 can make a two-dimensional relative movement within an x-y plane in FIG. 2, and further can make a three-dimensional relative movement including a z-direction. In the present exemplary embodiment, the moving mechanism 205 includes a motor such as a stepping motor that produces a driving force, a driving mechanism that transmits the driving force, and a position sensor that detects positional information of the probe 202. As the driving mechanism, a mechanism such as a lead screw mechanism, a link mechanism, a gear mechanism, or a hydraulic mechanism can be used. For the position sensor, a device such as a potentiometer using a component such as an encoder, a variable resistor, a linear scale, a magnetic sensor, an infrared sensor, or an ultrasonic sensor can be used. The present system can be of a handheld type, without including the moving mechanism 205. In the handheld type, a user operates the probe 202 while holding the probe 202.

The image reconstruction is performed using a photoacoustic signal acquired at a location where the relative position of the probe 202 with respect to the subject 210 is different. This can inhibit an artifact on an image obtained by the image reconstruction.

The apparatuses constituting the system according to the present exemplary embodiment that include the modality apparatus described above, can be configured of a separate piece of hardware or can all be configured of one piece of hardware. The function of the system according to the present exemplary embodiment can be configured of any type of hardware.

Units each having a calculation function in the system according to the present exemplary embodiment can be configured of a processor such as a central processing unit (CPU) or a graphics processing unit (GPU), or an arithmetic operation circuit such as a field programmable gate array (FPGA) chip. These units can be configured of a single processor or arithmetic operation circuit, or can be configured of a plurality of processors and arithmetic operation circuits.

The unit having a control function in the system according to the present exemplary embodiment is configured of a computing element such as a CPU. The unit having the control function controls the operation of each system. The unit having the control function can control each system in response to received instruction signals based on various operations such as start of measurement, from an input apparatus 105 such as a mouse or a keyboard. The unit having the control function controls the operation of each configuration of the modality apparatus by reading out a program code.

The display apparatus 104 is a display such as a liquid crystal display, an organic electro luminescence (EL) field emission display (FED), a glasses-type display, or a head mount display. The display apparatus 104 displays, for example, an image based on volume data, and a voxel value of a specific position. The display apparatus 104 can display a graphical user interface (GUI) for operating an apparatus or an image based on volume data. For the input apparatus 105, an operation console that can be operated by the user and is configured of components such as a mouse and a keyboard can be adopted. The display apparatus 104 can be configured of a touch panel serving as the input apparatus 105.

Transmission and reception of data can be performed by wire or wirelessly.

Figure 3:
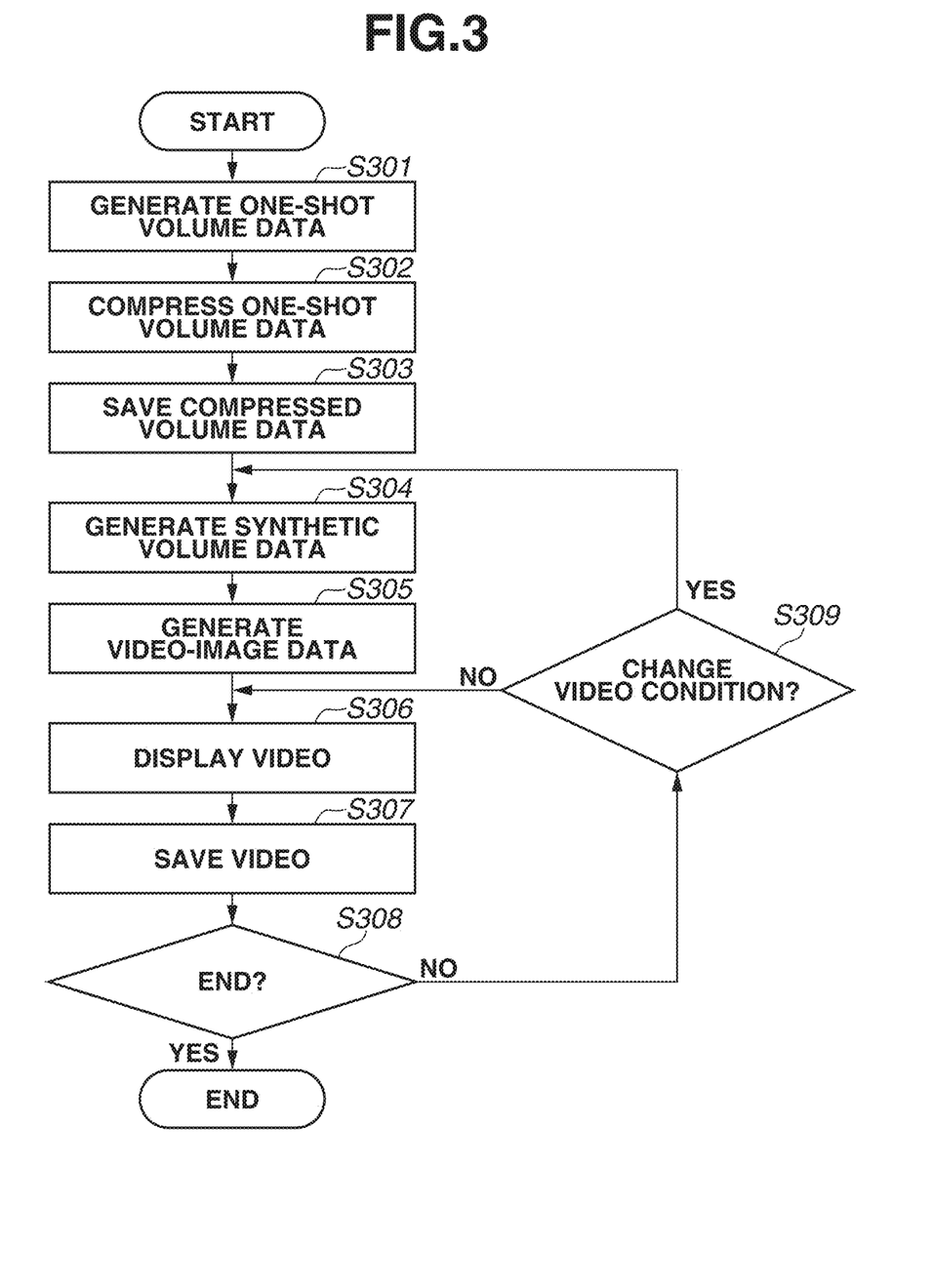
FIG. 3 is a flowchart representing an image processing method to be executed by the system according to the first exemplary embodiment.

A flow of an image processing method to be executed by the system according to the present exemplary embodiment will be described below. FIG. 3 is a flowchart representing the image processing method to be executed by the system according to the present exemplary embodiment. The following photoacoustic imaging apparatus in the present exemplary embodiment is mainly intended for diagnosis of a vascular disease or a malignant tumor of a person or an animal, and follow-up of chemotherapy. Therefore, the subject is assumed to be a part of a living body.

(Step S301: Process for Generating One-Shot Volume Data)

The modality apparatus 101 according to the present exemplary embodiment is the photoacoustic imaging apparatus, and acquires volume data by capturing an image of a subject. After the subject is set in a specified posture, the modality apparatus 101 irradiates the subject with light. The light is absorbed by an absorbent inside the subject, and a photoacoustic wave is produced from the absorbent. The probe of the modality apparatus 101 receives the produced photoacoustic wave.

The modality apparatus 101 serving as an image data generation unit executes image reconstruction processing using a reception signal of the photoacoustic wave received by the probe, and thereby generates volume data (three-dimensional medical image data). This image reconstruction processing is performed on the photoacoustic signal individually for each light irradiation. In the present specification, volume data corresponding to each light irradiation is referred to as "one-shot volume data".

Any scheme can be adopted for a reconstruction algorithm if the scheme can generate volume data including a negative value. Examples of the scheme include a back projection method in time domain, a back projection method in Fourier domain, and a model-based method (an iterative operation method). Examples of the back projection method in time domain for generating volume data including a negative value include universal back-projection (UBP), filtered back-projection (FBP), and phasing addition (delay-and-sum).

One-shot volume data reconstructed by the UBP or FBP has a negative value generated by differential processing. An artifact can be effectively inhibited by synthesizing a plurality of pieces of one-shot volume data including a negative value.

In the phasing addition, Hilbert transformation (in which a positive frequency component is advanced by 90 degrees and a negative frequency component is delayed by 90 degrees) is performed on a reception signal. Subsequently, envelope detection is performed, by calculating a phasing addition value for each voxel within a space, and determining the absolute value of this value. Here, the phasing addition value is a complex number, and a real part and an imaginary part can each be a negative value. Therefore, in this process, volume data configured of a phasing addition value before the envelope detection is referred to as "volume data including a negative value" so that the volume data including a negative value is used as a compression target in step S302 to be described below. In other words, in a case where image reconstruction is performed by the phasing addition, data compression according to the present exemplary embodiment is preformed on one-shot volume data configured of a phasing addition value. Further, in step S304 to be described below, synthesis processing is executed for the phasing addition value of each voxel of the one-shot volume data.

The one-shot volume data 1010 generated by the image generating unit 207 of the modality apparatus 101 is sent to the image processing apparatus 102.

(Step S302: Process for Compressing One-Shot Volume Data)

The image processing apparatus 102 reduces a data amount by compressing the one-shot volume data. The one-shot volume data according to the present exemplary embodiment has a negative value. In a case where ideal image capturing cannot be performed (e.g., where the probe 202 has a limited reception band), the number of voxels having a negative value and the number of voxels having a positive value are nearly equal. In such a case, the average value of all the voxels tends to be about 0. An artifact can be effectively cancelled by synthesizing a plurality of pieces of data thus having positive and negative values and having different artifact patterns. In a case where the threshold processing is performed on such data, it is necessary to consider not only the magnitude of a positive value, but also the magnitude of a negative value. Therefore, the image processing apparatus 102 performs data compression in consideration of the absolute value of each voxel of the one-shot volume data.

The one-shot volume data is configured of the coordinate value data of each voxel and voxel value data associated with the coordinate value. For example, the image processing apparatus 102 converts the voxel value data having positive and negative values into absolute value data. Next, the image processing apparatus 102 compares a predetermined threshold and the absolute value of each voxel, and extracts a voxel greater than the threshold and a coordinate value corresponding to this voxel. Afterward, the extracted voxel is returned to the original voxel value data. In other words, in a case where the original value is negative, the absolute value is converted into a negative value.

The image processing apparatus 102 can delete a voxel having a voxel value whose absolute value is less than the threshold, and the coordinate value data corresponding to this voxel, in the compression processing. Alternatively, the image processing apparatus 102 can overwrite the voxel value of a target voxel with 0. In this case, the image processing apparatus 102 can compress data by applying various types of encoding processing such as a run length method. The method for compressing data is not limited to the run length method, and any scheme for performing compression utilizing redundancy and regularity of data can be used. In this processing, the data having the value less than the threshold is deleted or overwritten, and therefore, lossy compression processing is adopted. However, an appropriate threshold can be selected as long as an image is compressed to the extent that deterioration of an image cannot be visually recognized. A voxel having a voxel value equal to the threshold can be handled as an extraction target, or can be handled as a data-amount reduction target.

In a case where the one-shot volume data is configured of 500×500×500 voxels, the data size is about 500 MB. In a case where a video is captured for one minute with a repetition frequency of 10 Hz, the number of piece of one-shot volume data to be generated is 600, and the total data size is about 300 GB. Although depending on the regularity of the original data, the total data size can be compressed to about 30 GB, in a case where 10% of all voxels is extracted by the threshold processing.

The volume data after being subjected to the compression processing in this process is referred to as "compressed volume data". Here, assuming that the threshold processing for extracting a target voxel considering the absolute value of a voxel value is one of compression processes, data at a stage where the threshold processing is performed on the one-shot volume data is also referred to as the compressed volume data.

Compression can be similarly performed, by setting the first threshold that is the positive value and the second threshold that is the negative value, and extracting a voxel having a voxel value greater than the first threshold that is positive and a voxel having a voxel value less than the second threshold that is negative, as described above. For example, the image processing apparatus 102 can set the first threshold and the second threshold such that the number of positive voxels and the number of negative voxels are equal.

The image processing apparatus 102 can set one threshold for all pieces of one-shot volume data to be used for one video. In other words, the same threshold can be applied to the entire one-shot volume data set that is used for video generation. The voxel values can be prevented from varying among frames of the video to be generated, by thus specifying the same threshold for all the data.

Further, the image processing apparatus 102 can perform the compression processing by setting a threshold that is different for each piece of one-shot volume data or each piece of synthetic volume data. In this case, a window level can be optimized for each frame of the video to be generated. Even if a voxel-value difference between frames is large, it is possible to generate the compressed volume data that enables generation of an image of optimum image quality for each frame.

The image processing apparatus 102 can determine a voxel value that corresponds to an absolute value at the position of a predetermined number in descending order from the top, among the absolute values of the voxel values of pieces of volume data (a volume data set), as a threshold common to each piece of the volume data. Further, the image processing apparatus 102 can determine a value that corresponds to an absolute value at the position of a predetermined number in descending order from the top, among the absolute values of the voxel values, as a threshold, for each of piece of volume data. For example, a number corresponding to 10% of the number of voxels of target volume data can be set as the predetermined number. The image processing apparatus 102 can acquire information about the predetermined number via the input apparatus 105. The user can input the predetermined number itself, or information (such as a ratio to the total number of voxels) that enables determination of the predetermined number, as the information about the predetermined number, using the input apparatus 105. The image processing apparatus 102 can read out the information about the predetermined number from the storage apparatus 103. In a case where the first threshold and the second threshold are to be set, a first predetermined number for positive voxel values and a second predetermined number for negative voxel values can be different. Further, a value corresponding to the first predetermined number in descending order from the top among the positive voxel values can be the first threshold, and a value corresponding to the second predetermined number in descending order from the top among the negative voxel values can be the second threshold.

The image processing apparatus 102 can set a threshold, based on a measurement value of intensity of light with which the photoacoustic imaging apparatus irradiates a subject. A photoelectric conversion element such as a photodiode can be used for the measurement of the light intensity of the irradiation light.

For example, a reference value for a threshold when the light intensity of irradiation light is at a reference value, is determined beforehand. The image processing apparatus 102 can then determine a threshold to be used for the threshold processing, by multiplying or dividing the reference value for the threshold by the ratio between the reference value for the light intensity and a measurement value.

The image processing apparatus 102 can read out a table or expression that represents a relationship between light intensity and threshold, and determine a threshold corresponding to a measurement value of a light intensity of irradiation light, based on the table or expression.

By thus determining the threshold based on the intensity of the irradiation light, a threshold suitable for each of a plural times of light irradiation can be adaptively set.

In a case where the first threshold and the second threshold are set, the first threshold and the second threshold can be determined by different methods. For example, a value that corresponds to a voxel value whose absolute value at the position of a predetermined number in descending order from the top can be determined, as to at least one of the first threshold and the second threshold. Further, at least one of the first threshold and the second threshold can be determined based on a light intensity of irradiation light.

In the present exemplary embodiment, the example in which the modality apparatus 101 generates the volume data is described. However, the volume data can be generated beforehand, and the image processing apparatus 102 can acquire the generated data by reading outing the volume data as a compression target from the storage apparatus 103.

(Step S303: Process for Saving Compressed Volume Data)

The image processing apparatus 102 saves the compressed volume data in the storage apparatus 103. In a case where the storage apparatus 103 is the PACS, the image processing apparatus 102 saves the compressed volume data through a network. Because the one-shot volume data is compressed, it is possible to reduce a load on the storage apparatus 103 and a load put on communications in the network.

The image processing apparatus 102 can save the compressed volume data in association with image-capturing information provided as supplementary information, in the storage apparatus 103. The image-capturing information is, for example, patient identification information such as a patient full name, a date of birth, gender, and information about an examination date, a body part subjected to image capturing, and an apparatus parameter (a light irradiation pattern) of the modality apparatus 101 at the time of image capturing.

The image processing apparatus 102 can save the compressed volume data in the storage apparatus 103, in data format conforming to Digital Imaging and Communications in Medicine (DICOM). In other words, the image processing apparatus 102 can save DICOM data including the compressed volume data and the supplementary information in the storage apparatus 103.

The one-shot volume data before the compression can be deleted from the storage apparatus 103, when generation of the compressed volume data is completed. Alternatively, the one-shot volume data can be deleted based on an instruction to delete the one-shot volume issued by the user after the compressed volume data is confirmed by the user. A data amount in the storage apparatus 103 can be reduced by thus deleting the one-shot volume. The compressed volume data is in such a state that almost none of useful information is lost. Therefore, the useful information can be reproduced from the compressed volume data even if the one-shot volume is deleted.

(Step S304: Process for Generating Synthetic Volume Data)

The image processing apparatus 102 generates synthetic volume data, by reading out a plurality of pieces of one-shot volume data compressed in step S302 from the storage apparatus 103, and synthesizing these pieces of one-shot volume data. The image processing apparatus 102 performs synthesis processing, after restoring the compressed volume data as necessary to perform the synthesis processing. For example, in a case where an arithmetic operation cannot be directly performed on the pieces of volume data after the compression by encoding processing, the volume data at a stage where the threshold processing is applied is restored by restoration processing and the restored volume data is synthesized. When restoring the volume data from the compressed volume data, the image processing apparatus 102 can use the supplementary information associated with the compressed volume data. For example, the image processing apparatus 102 can perform the restoration processing, using the image-capturing information (information such as a voxel pitch) associated as the supplementary information. Further, the image processing apparatus 102 can determine compressed volume data to be a synthesis target, using the image-capturing information (information such as light irradiation timing and a wavelength of light) associated as the supplementary information, and can perform the synthesis processing for this synthesis target.

The image processing apparatus 102 can perform synthesis by, for example, adding, averaging, or arithmetic-geometric averaging of the compressed volume data. The synthetic volume data in which an artifact is inhibited is generated by these types of processing. In a case where volume data is derived from a photoacoustic wave, the image processing apparatus 102 can acquire spectral information, by synthesizing a plurality of pieces of compressed volume data corresponding to a plurality of wavelengths generated by light irradiation of wavelengths different from each other. As an example, a case will be described where a spatial distribution of oxygen saturation is acquired as the spectral information, using compressed volume data that indicates a spatial distribution of absorption coefficients corresponding to light of two wavelengths. In this case, the image processing apparatus 102 can perform synthesis processing for acquiring oxygen saturation $SO_2$ based on the following expression (1).

$$SO_2 = \frac{\frac{\mu_a(\lambda_2)}{\mu_a(\lambda_1)} \cdot \varepsilon_{de}(\lambda_1) - \varepsilon_{de}(\lambda_2)}{(\varepsilon_{ox}(\lambda_2) - \varepsilon_{de}(\lambda_2)) - \frac{\mu_a(\lambda_2)}{\mu_a(\lambda_1)} \cdot (\varepsilon_{ox}(\lambda_1) - \varepsilon_{de}(\lambda_1))} \quad (1)$$

Here, $\mu_a$ represents an absorption coefficient [mm$^{-1}$], $\varepsilon_{ox}$ represents a molar absorption coefficient [mm$^{-1}$ mol$^{-1}$] of oxyhemoglobin, and $\varepsilon_{de}$ represents a molar absorption coefficient [mm$^{-1}$ mol$^{-1}$] of deoxyhemoglobin. ($\lambda$1) is an index for representing a parameter corresponding to light of a first wavelength, and ($\lambda$2) is an index for representing a parameter corresponding to light of a second wavelength.

Figure 4:
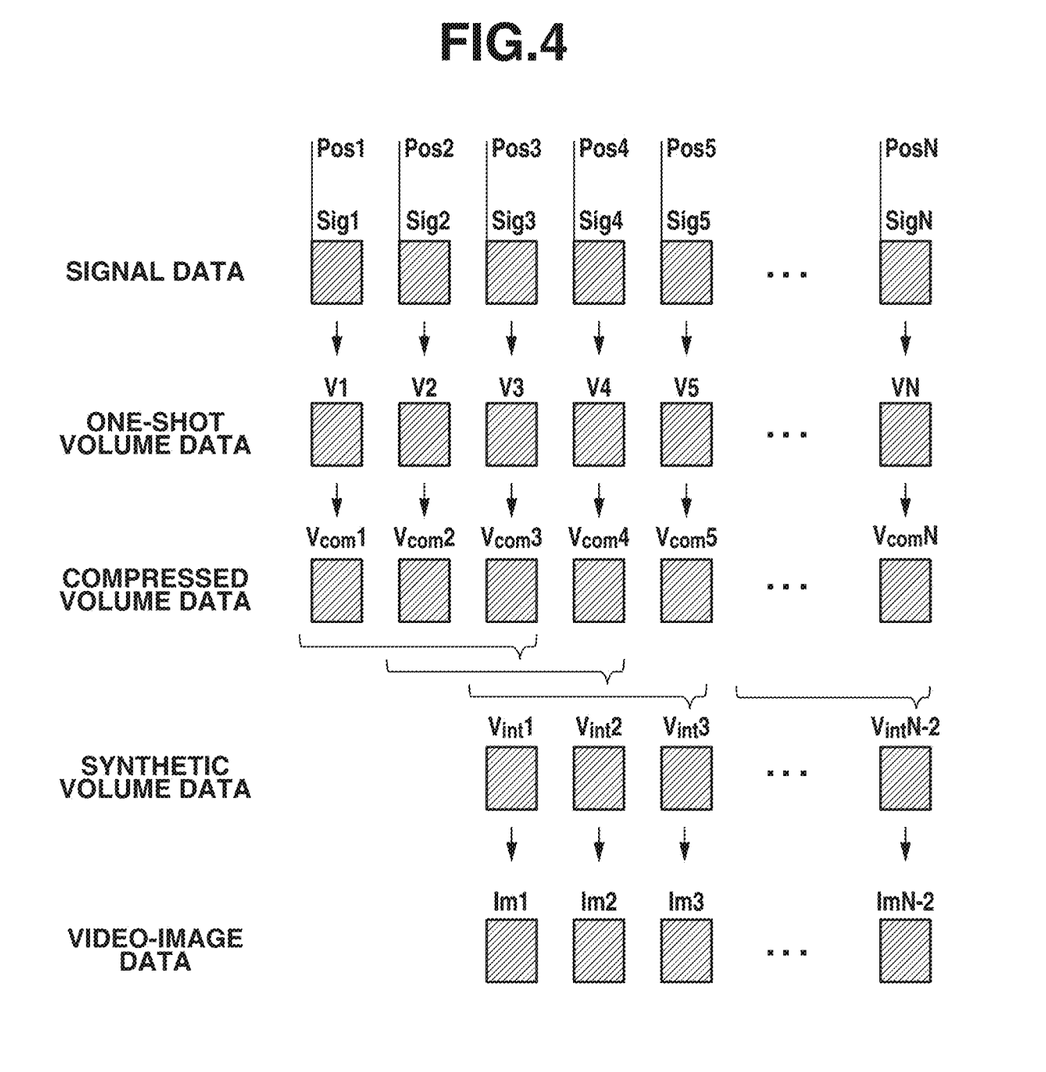
FIG. 4 is a data flowchart according to the first exemplary embodiment.

A relationship of data processing to be performed by the signal receiving unit 206, the image generating unit 207, and the image processing apparatus 102 will be described below with reference to FIG. 4. Pieces of photoacoustic signal data acquired when the relative positions between the subject and the probe are Pos1, Pos2, Pos3, . . . , and PosN, are indicated by Sig1, Sig2, Sig3, . . . , and SigN. The signal receiving unit 206 acquires a photoacoustic signal derived from a photoacoustic wave received at each of the relative positions. The image generating unit 207 generates pieces of one-shot volume data V1, V2, . . . , and VN, by performing image reconstruction using the photoacoustic signal. Further, the image processing apparatus 102 compresses the one-shot volume data, and thereby generates compressed volume data $V_{com}1$, $V_{com}2$, . . . , and $V_{com}N$. Furthermore, the image processing apparatus 102 generates synthetic volume data $V_{int}1$, $V_{int}2$, . . . , and $V_{int}N-2$, using a plurality of pieces of compressed volume data. FIG. 4 illustrates an example in which one piece of synthetic volume data is generated by synthesizing three pieces of compressed volume data. An image in which an artifact is inhibited can be generated by synthesizing the plural pieces of one-shot volume data that respectively correspond to the different relative positions between the subject and the probe. In addition, because the compression is performed in consideration of the absolute value of a voxel, the volume data after the compression also includes a voxel having a negative value. Therefore, as described above, when a plurality of pieces of volume data are synthesized, image degradation can be reduced, as compared with a compression method not considering a negative value.

The smaller the number of pieces of one-shot volume data to be used for the generation of synthetic volume data, the higher the temporal resolution of an image that can be obtained. In contrast, the larger the number of pieces of one-shot volume data to be used for the generation of synthetic volume data, the higher the signal-to-noise ratio of an image that can be obtained. Here, in a case where a video is generated for the first time after image capturing, a default value set beforehand is used as the number of pieces of one-shot volume data to be synthesized. For example, a default number of syntheses can be determined beforehand to have a frame rate of 1 Hz or more. In a case where the repetition frequency of light emission by the light source 204 is 10 Hz, 10 or less can be set as the default number of syntheses. The user can change the number of syntheses or the combination of pieces of volume data to be synthesized, using the input apparatus 105, by confirming an image based on the synthetic volume data generated based on the default number of syntheses. The image processing apparatus 102 can acquire information indicating the number of syntheses or the combination of pieces of volume data via the input apparatus 105, and change the combination of pieces of one-shot volume to be used for generation of a synthetic volume, based on the acquired information.

(Step S305: Process for Generating Video-image Data)

The image processing apparatus 102 generates two-dimensional video image data, by rendering the three-dimensional synthetic volume data generated in step S304. The two-dimensional video image data corresponds to one frame of a video. The image processing apparatus 102 performs rendering on a plurality of pieces of synthetic volume data to generate a two-dimensional image data set in which pieces of data are arranged in chronological order, as the video-image data. In other words, the image processing apparatus 102 generates pieces of two-dimensional video image data Im1, Im2, ..., and ImN−2, from the pieces of synthetic volume data $V_{int}1$, $V_{int}2$, ..., and $V_{int}N-2$.

For a rendering scheme, any method can be used. Examples of the method include a maximum projection method (maximum intensity projection (MIP)), volume rendering, and surface rendering. Here, setting conditions, such as an area and a line of sight, in rendering the three-dimensional synthetic volume data into the two-dimensional image can be freely set to be suitable for an observation target.

To summarize the operation described thus far, in the present exemplary embodiment, a photoacoustic signal at each of N points (N is an integer of 3 or more) corresponding to the different relative positions to the subject is acquired, and thereby N pieces of one-shot volume data are obtained. Subsequently, at least two pieces are synthesized among from i-th to (i+m)-th one-shot volume data (i+m<N; "i" and "m" are both natural numbers), to generate the first synthetic volume data. Further, at least two pieces are synthesized among from (i+n)-th to (i+n+m)-th one-shot volume data ("n" is a natural number) to generate the second synthetic volume data. In other words, a plurality of pieces of synthetic volume data is generated by synthesizing a plurality of pieces of volume data in mutually different combinations.

(Step S306: Process for Displaying Video)

The image processing apparatus 102 displays a video based on the video-image data generated in step S305, on the display apparatus 104. In other words, the display apparatus 104 sequentially updates each image based on the video-image data and displays the updated image. For example, the image processing apparatus 102 updates the displayed image from a first synthetic image based on the first synthetic volume data to a second synthetic image based on the second synthetic volume data, and thereby sequentially displays the first synthetic image and the second synthetic image.

(Step S307: Process for Saving video)

In a case where an instruction to save a video is received from the user, the image processing apparatus 102 saves the video-image data corresponding to the video displayed on the display apparatus 104 in the storage apparatus 103. The user can specify a start frame and an end frame of a saving target, using the input apparatus 105. The image processing apparatus 102 can determine a frame to be saved in the storage apparatus 103 from the video-image data, by acquiring information indicating the frame to be saved, via the input apparatus 105.

In a case where the user confirms the displayed video and determines that a desired video has been obtained, the user can issue an instruction to save the video, using the input apparatus 105. For example, the user can confirm a signal-to-noise ratio and time variations of an observation target, and thereby determine whether a desired video has been obtained.

The image processing apparatus 102 can save the video-image data in data format conforming to DICOM, in the storage apparatus 103.

(Step S308: Process for Determining Whether to End Image Processing)

The image processing apparatus 102 determines whether to end the image processing. For example, the image processing apparatus 102 can end the image processing in a case where an end instruction is received from the user (YES in step S308). The image processing apparatus 102 can end the image processing in a case where information indicating completion of the saving of the video is received. Ending the image processing is equivalent to ending the display of the video. In a case where the image processing is not to be ended (NO in step S308), the processing proceeds to step S309.

In the present exemplary embodiment, the example is described in which whether to end the image processing is determined after the video is saved. However, the image processing can end without saving the video.

(Step S309: Process for Determining Whether to Change video Condition)

In a case where the user determines that the video condition needs to be changed, the user can give an instruction to change the video condition, using the input apparatus 105. The image processing apparatus 102 can reset the video condition in a case where information indicating the changed video condition is received via the input apparatus 105 (YES in step S309). The processing then returns to the process for generating the synthetic volume data in step S304, and performs the video generation again. In a case where there is no instruction to change the video condition (NO in step S309), the video display based on the already-set video condition continues.

For example, the image processing apparatus 102 can change the number of pieces of one-shot volume data to be used for the synthetic volume data, or a video rendering condition (an imaging area, an MIP conversion direction, or a gradation setting) of the video-image data, as the video condition. In a case where the rendering condition is to be changed as the video condition, it is not necessary to generate the synthetic volume data again, and therefore, the processing can return from step S309 to step S305.

It is possible that the user determines the number of pieces of volume data to be used for the generation of the synthetic volume data, considering that the signal-to-noise ratio and the temporal resolution of the synthetic volume data are determined based on the number of pieces of volume data to be synthesized. The display apparatus 104 can enhance the convenience of the user, by displaying a synthetic volume image when the number of pieces of volume data to be used for synthesis is changed, together with the number of syntheses for such a synthetic volume image. The larger the number of pieces of volume data to be used for synthesis, the higher the artifact reduction effect and the system-noise reduction effect, and thus, a synthetic volume image of high image quality can be confirmed. However, the temporal resolution decreases. Therefore, an acquisition duration of a photoacoustic signal being used for synthesis or a refresh period (Hz) of a video based on the acquisition duration can be calculated, and the result of this calculation can be displayed. The user can thereby recognize the temporal resolution of an image to be obtained, and can easily specify the number of pieces of volume data to be used for synthesis.

The user can perform the series of specifying such operations, by operating a GUI displayed by the display apparatus 104.

As described above, according to the system of the present exemplary embodiment, it is possible to reduce a load put on a storage, communications, and image processing, by appropriately compressing the volume data for video generation having a large data volume.

Because the compressed volume data is saved, generation of a desired video can be performed again by changing the condition for generating the video after the series of processes up to the video generation described in the present exemplary embodiment is completed.

Figure 5:
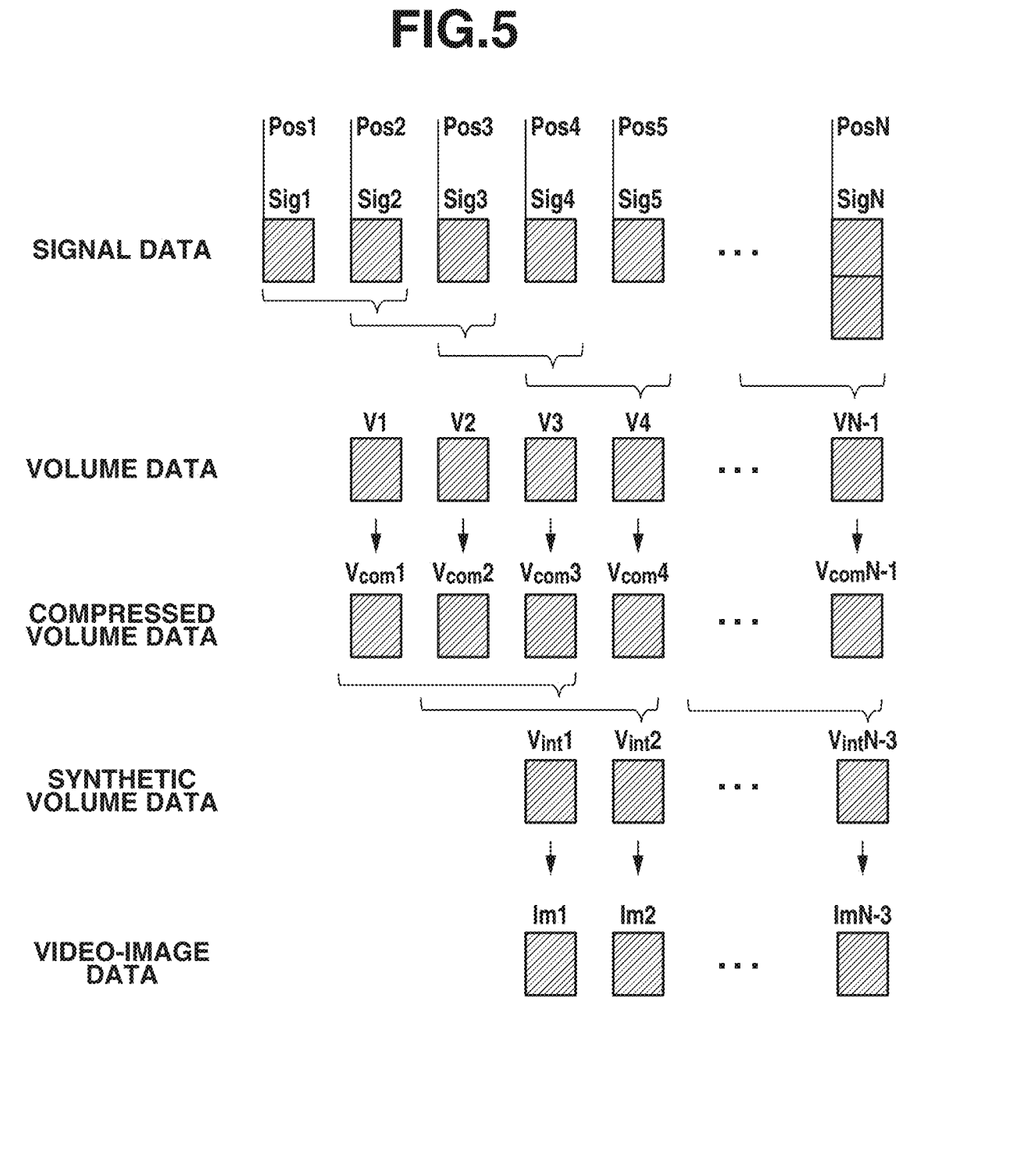
FIG. 5 is another data flowchart according to the first exemplary embodiment.

In the present exemplary embodiment, the example in which the compression target is the one-shot volume data is described. However, the compression target can be any type of volume data if the volume data includes a negative value. For example, as illustrated in FIG. 5, the compression target can be volume data including a negative value and generated by synthesizing pieces of signal data corresponding to a plurality of times of light irradiation. In the example illustrated in FIG. 5, the image processing apparatus 102 generates the volume data V1 to VN−1 including a negative value, by synthesizing pieces of signal data corresponding to two times of light irradiation. The image processing apparatus 102 generates pieces of compressed volume data to $V_{com}1$ to $V_{com}N-1$ by compressing the volume data V1 to VN−1, and saves the generated compressed volume data in the storage apparatus 103. The image processing apparatus 102 generates synthetic volume data $V_{int}1$ to $V_{int}N-3$, by reading out three pieces of compressed volume data from the storage apparatus 103, and synthesizing the read-out compressed volume data. The image processing apparatus 102 generates video-image data Im1 to ImN−3 from the respective pieces of synthetic volume data $V_{int}1$ to $V_{int}N-3$, and saves the generated video-image data in the storage apparatus 103. FIG. 5 illustrates the example in which the pieces of signal data corresponding to the plurality of times of light irradiation are synthesized. However, synthetic volume data including a negative value can be generated by synthesizing a plurality of pieces of one-shot volume data corresponding to times of light irradiation, and the generated synthetic volume data can be used as the compression target. Also in this case, volume data in which an artifact is inhibited can be generated by further synthesizing the compressed pieces of synthetic volume data. The data amount of the compressed volume data to be saved in the storage apparatus 103 can be thereby further inhibited.

The number of times of light irradiation and the combination of light irradiation that correspond to the volume data to be used as the compression target can be changeable. The number of times of light irradiation and the combination of light irradiation can be changed based on input by the user, or can be changed depending on an image-capturing mode.

Figure 6:
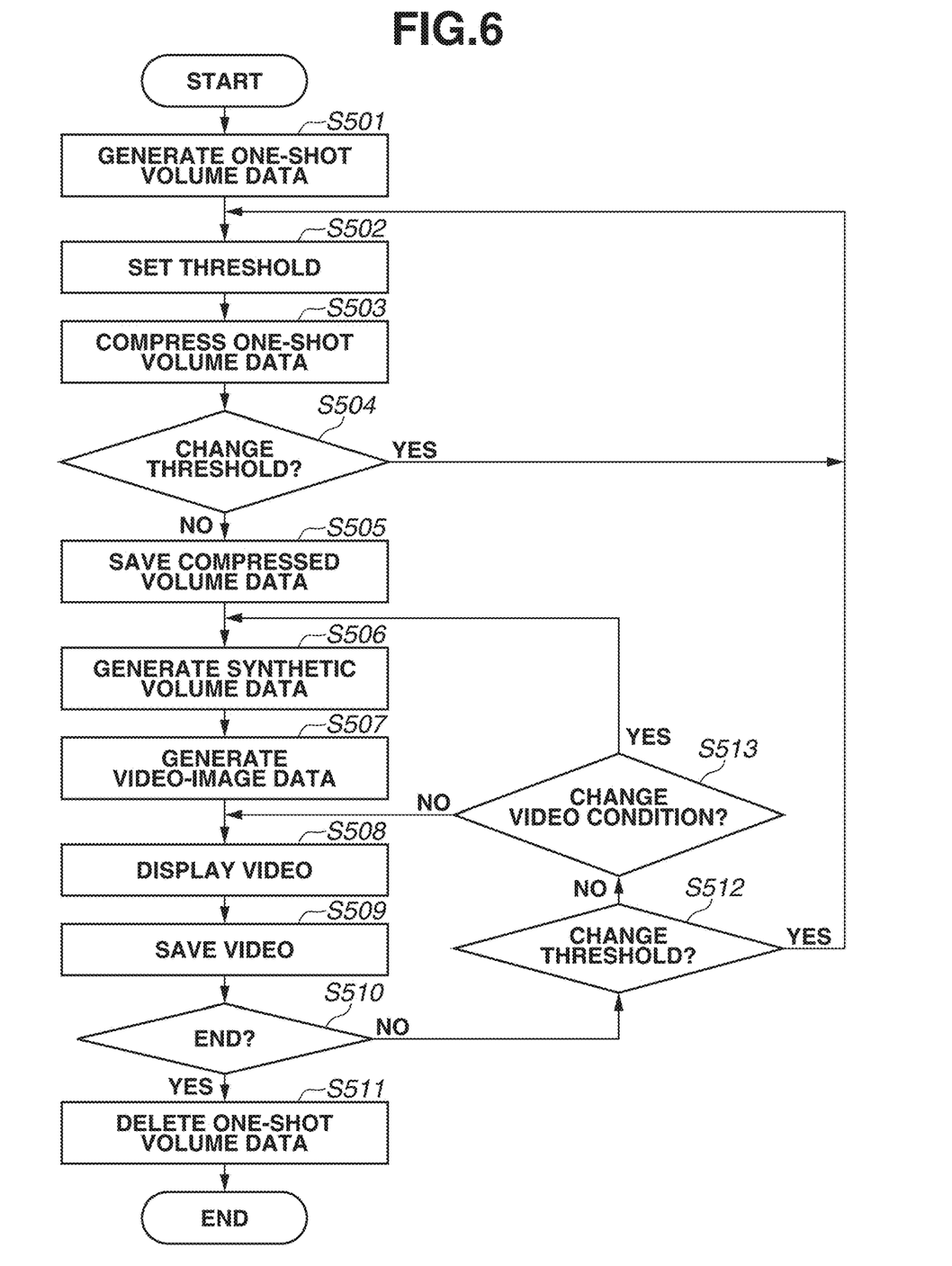
FIG. 6 is a flowchart representing an image processing method to be executed by a system according to a second exemplary embodiment.

In the first exemplary embodiment, the example has been described in which the threshold to be used for the compression processing is a value set beforehand. In a second exemplary embodiment, an example in which a threshold is reset after a user confirms a video will be described. FIG. 6 illustrates a flowchart up to moving-image generation in the present exemplary embodiment. Step S501 step S503, step S505 to step S510 and step S513 in FIG. 5 correspond to step S301, step S302, step S303 to step S308, and step S309 in FIG. 3, respectively. Here, a difference from the first exemplary embodiment will be mainly described.

(Step S502: Process for Setting Threshold)

The image processing apparatus 102 sets a threshold to be used for threshold processing which is applied to one-shot volume data. The image processing apparatus 102 sets the threshold corresponding to the absolute value of a voxel value, or the first threshold for positive voxel values and the second threshold for negative voxel values described in the first exemplary embodiment.

For example, the user can specify the threshold, using the input apparatus 105. For this specification of the threshold, the image processing apparatus 102 can collect the absolute values of the voxel values of all pieces of one-shot volume data to be used for a video, and arrange the collected absolute values in order of the magnitude of absolute value. The image processing apparatus 102 can then display information representing the collected voxel values as a histogram on the display apparatus 104. The display apparatus 104 can display the histogram, a compression rate corresponding to the specified threshold, and the data size of each of the original data and the compressed data, in combination. The user can specify any threshold, by confirming these display information, and taking the expected image quality of an observation target and the compression rate of data into consideration.

Further, the image processing apparatus 102 can display a histogram of the voxel values of specific one-shot volume data on the display apparatus 104. Furthermore, the image processing apparatus 102 can display a histogram of the voxel values of specific synthetic volume data on the display apparatus 104. The image processing apparatus 102 can also display a histogram of the voxel values of synthetic volume data obtained by synthesizing all pieces of one-shot volume data to be used for a video, on the display apparatus 104. The image processing apparatus 102 can also display a histogram of voxel values included in a specific area within specific one-shot volume data on the display apparatus 104. In a case where variations in sensitivity that are unique to an apparatus are present in one-shot volume data, the image processing apparatus 102 can display a histogram of the voxel values of voxels present within a high-sensitivity area, on the display apparatus 104. In this case, an area in which sensitivity unique to the apparatus is higher than a predetermined threshold can be used as the high-sensitivity area. The user can specify the threshold based on these pieces of display information.

The image processing apparatus 102 can set one threshold for all pieces of one-shot volume data to be used for one video. In other words, the same threshold can be applied to the entire one-shot volume data set that is to be used for video generation. It is possible to prevent voxel values from varying between the frames of a video to be generated, by thus specifying the same threshold for all the data.

Further, the image processing apparatus 102 can set a different threshold for each one-shot volume data or each synthetic volume data, and perform the compression processing based on the set threshold. In this case, a window level can be optimized for each frame of a video to be generated. Even if a voxel-value difference between frames is large, it is possible to generate the compressed volume data that enables generation of an image of optimum quality for each frame.

Further, the user can specify the first threshold for positive voxel values and the second threshold for negative voxel values, using the input apparatus 105 in a manner similar to the above-described specification of the threshold. The image processing apparatus 102 can acquire information indicating the first threshold and the second threshold via the input apparatus 105. The user can specify at least one of the first threshold and the second threshold.

In the first exemplary embodiment, the threshold can be specified in a manner similar to this process as well. Further, in the present exemplary embodiment, the threshold can be determined in a manner similar to the manner described in the first exemplary embodiment as well, when the threshold is initially set. In other words, the threshold can be determined by the image processing apparatus 102 when the threshold is initially set, and the threshold can be determined based on an instruction of the user when the threshold is set next.

(Step S504: Process for Determining Whether to Change Threshold)

The image processing apparatus 102 converts the one-shot volume data that is compressed according to the set threshold into an image, and displays the image on the display apparatus 104. The various rendering schemes described above can be used for a scheme of this conversion. At this moment, the image processing apparatus 102 can display a message asking whether to save the compressed volume data on the display apparatus 104. The user confirms the displayed image, and gives an instruction to change the threshold in a case where the user determines that the threshold needs to be changed. In a case where information indicating the threshold change is received via the input apparatus 105 (YES in step S504), the processing returns to step S502 in which the user is prompted to specify the threshold again. In a case where there is no instruction for a threshold change from the user (NO in step S504), the processing proceeds to step S505.

In the present exemplary embodiment, the example in which the threshold is specified is described. However, such specification is not limited to the threshold, and other factors such as a compression rate can be specified as long as the degree of the compression of volume data can be changed. When the compression rate is specified, the image processing apparatus 102 can search for a threshold that can realize the specified compression rate, and determine the threshold corresponding to the specified compression rate.

In a case where the user confirms the displayed video in step S508 and determines that the threshold needs to be changed, the user can give an instruction to change the threshold, using the input apparatus 105. In a case where the image processing apparatus 102 receives information indicating a threshold change via the input apparatus 105 (YES in step S512), the processing returns to step S502. In a case where no instruction for a threshold change is received (NO in step 512), the processing proceeds to step S513. In step S513, in a manner similar to step S309, the image processing apparatus 102 determines whether the video condition has been changed. In a manner similar to step S309, the image processing apparatus 102 can reset the video condition based on the information indicating the video condition received via the input apparatus 105. In a case where the image processing apparatus 102 receives no instruction to change the video condition (NO in step S513), the display of the video generated based on the already-set video condition continues.

In the present exemplary embodiment, the determination of the video condition change in step S513 is performed after the determination of the threshold change is made in step S512. However, these steps can be performed in reverse order. Further, only one of these steps can be executed. In other words, at least one of step S512 and step S513 can be executed.

(Step S511: Process for Deleting One-Shot Volume Data)

In a case where the image processing apparatus 102 determines to end the image processing in step S510 (YES in step S510), the image processing apparatus 102 deletes the one-shot volume data held in the storage apparatus 103. Upon the deletion of the one-shot volume data, the image processing ends. As a result of this processing, only the compressed one-shot volume data remains as the saved data, so that a load on the storage apparatus can be reduced. In the second exemplary embodiment, the compression target is not limited to the one-shot volume similar to the first exemplary embodiment.

As described above, according to the system of the present exemplary embodiment, it is possible to reduce a load on a storage, communications, and image processing, by appropriately compressing the volume data for video generation having a large data volume.

Other Embodiments

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2018-023554, filed Feb. 13, 2018, which is hereby incorporated by reference herein in its entirety.

What is claimed is:

1. An image processing apparatus comprising:
a processor; and
a memory storing a program which, when executed by the processor, causes the image processing apparatus to:
acquire a plurality of pieces of volume data including a negative voxel value and derived from a photoacoustic wave produced by irradiating a subject with light, wherein the plurality of pieces of volume data are acquired at different positions for light irradiation;
generate a plurality of pieces of compressed volume data by compressing the plurality of pieces of volume data to reduce a data amount of voxel data having a voxel value whose absolute value is less than a threshold;
save the plurality of pieces of compressed volume data into a storage;
read out the plurality of pieces of compressed volume data from the storage; and
generate composite volume data by combining the plurality of pieces of the compressed volume data.

2. The image processing apparatus according to claim 1, wherein the image processing apparatus is further caused to read out a plurality of pieces of the saved compressed volume data, and
wherein the image processing apparatus is further caused to generate synthetic volume data by synthesizing the plurality of pieces of the compressed volume data.

3. The image processing apparatus according to claim 2, wherein the image processing apparatus is further caused to generate a plurality of pieces of the composite volume data by combining the plurality of pieces of the compressed volume data in mutually different combinations.

4. The image processing apparatus according to claim 3, wherein the image processing apparatus is further caused to generate a plurality of synthetic images by performing maximum intensity projection for each of the synthetic volume data in a specific direction, and
wherein the image processing apparatus is further caused to display each of the synthetic images.

5. The image processing apparatus according to claim 1, wherein the image processing apparatus is further caused to determine the threshold based on an intensity of light with which the subject is irradiated.

6. The image processing apparatus according to claim 1, wherein the image processing apparatus is further caused to generate the volume data by universal back-projection image reconstruction processing, filtered back-projection image reconstruction processing, or phasing addition image reconstruction processing.

7. The image processing apparatus according to claim 1, wherein the image processing apparatus is further caused to save the compressed volume data and image-capturing information in association with each other.

8. The image processing apparatus according to claim 1, wherein the image processing apparatus is further caused to generate the compressed volume data by compressing the volume data by deleting voxel data having a voxel value whose absolute value is less than a threshold.

9. The image processing apparatus according to claim 1, wherein the image processing apparatus is further caused to generate the compressed volume data by compressing the volume data using a compression method based on redundancy of voxel data having a voxel value whose absolute value is less than a threshold.

10. The image processing apparatus according to claim 1, wherein the image processing apparatus is further caused to generate the compressed volume data by compressing the volume data without reducing a data amount of a voxel having a voxel value whose absolute value is greater than a threshold.

11. An image processing method comprising:
acquiring a plurality of pieces of volume data including a negative voxel value and derived from a photoacoustic wave produced by irradiating a subject with light wherein the plurality of pieces of the volume data are acquired at different positions for light irradiation;
generating a plurality of pieces of compressed volume data by compressing the plurality of pieces of the volume data to reduce a data amount of voxel data having a voxel value whose absolute value is less than a threshold;
saving the plurality of pieces of compressed volume data into a storage;
reading out the plurality of pieces of compressed volume data from the storage; and
generating composite volume data by combining the plurality of pieces of compressed volume data in mutually different combinations.

12. An image processing apparatus comprising:
a processor; and
a memory storing a program which, when executed by the processor, causing the image processing apparatus to:
acquire volume data including a negative voxel value and derived from a photoacoustic wave produced by irradiating a subject with light;
generate compressed volume data by compressing the volume data to reduce a data amount of voxel data having a voxel value whose absolute value is less than a threshold based on an intensity of light with which the subject is irradiated; and
save the compressed volume data into a storage.

13. An image processing method comprising:
acquiring volume data including a negative voxel value and derived from a photoacoustic wave produced by irradiating a subject with light;
generating compressed volume data by compressing the volume data to reduce a data amount of voxel data having a voxel value whose absolute value is less than a threshold based on an intensity of light with which the subject is irradiated; and
saving the compressed volume data into a storage.

* * * * *